United States Patent [19]
Petrille et al.

[11] Patent Number: 5,900,157
[45] Date of Patent: May 4, 1999

[54] METHODS FOR CONTROLLING MACROINVERTEBRATES IN AQUEOUS SYSTEMS

[75] Inventors: Joseph C. Petrille, North Wales; Michael W. Werner, Warrington, both of Pa.

[73] Assignee: BetzDearborn Inc., Trevose, Pa.

[21] Appl. No.: 08/896,780

[22] Filed: Jul. 18, 1997

[51] Int. Cl.[6] .................................................. C02F 1/50
[52] U.S. Cl. ..................... 210/755; 210/749; 210/764; 514/642
[58] Field of Search .................................. 210/749, 755, 210/698, 701, 764, 730; 514/642

[56] References Cited

U.S. PATENT DOCUMENTS

| | | | |
|---|---|---|---|
| 2,906,595 | 9/1959 | Pelcak et al. | 21/2.7 |
| 3,142,615 | 7/1964 | Wehner | 167/22 |
| 4,328,638 | 5/1982 | Smithson | 210/747 |
| 4,462,914 | 7/1984 | Smith | 210/755 |
| 4,561,983 | 12/1985 | Davis et al. | 210/755 |
| 4,579,665 | 4/1986 | Davis et al. | 210/755 |
| 5,015,395 | 5/1991 | Muia et al. | 210/755 |
| 5,096,601 | 3/1992 | Muia et al. | 210/755 |
| 5,118,346 | 6/1992 | Wehner et al. | 106/18.3 |
| 5,128,050 | 7/1992 | Gill | 210/755 |
| 5,192,451 | 3/1993 | Gill | 210/755 |
| 5,468,739 | 11/1995 | Whitekettle et al. | 514/75 |
| 5,643,462 | 7/1997 | Chen et al. | 210/730 |

FOREIGN PATENT DOCUMENTS

| | | |
|---|---|---|
| 1287573 | 4/1987 | Canada . |
| 549006 | 6/1993 | European Pat. Off. . |
| 0630858 | 12/1994 | European Pat. Off. . |

OTHER PUBLICATIONS

Smith et al., "Clams—A Growing Threat to Implant Water Systems", Plant Engineering, Jun. 14, 1979.
"Proceedings, First International Corbicula Symposium", J. C. Britton, ed., Texas Christian University, Oct. 1977.
21 CFR §176.300.
"Condensed Tannin for Adhesives", A. Pizzi, Ind. Eng. Chem. Prod. Res. Dev. 1982, 21, pp. 359–369.

*Primary Examiner*—Peter A. Hruskoci
*Attorney, Agent, or Firm*—Alexander D. Ricci; Phllip H. Von Neida

[57] ABSTRACT

Methods for controlling the fouling potential of macroinvertebrates are provided. An effective controlling amount of a polymer comprising a tannin and a cationic monomer is added to an aqueous system suffering from the fouling potential of macroinvertebrates.

12 Claims, No Drawings

METHODS FOR CONTROLLING MACROINVERTEBRATES IN AQUEOUS SYSTEMS

FIELD OF THE INVENTION

The present invention relates to methods for controlling fouling by macroinvertebrates, such as mollusks, in aqueous systems.

BACKGROUND OF THE INVENTION

Cooling systems for both industrial plants and utilities are subject to fouling by macroinvertebrates (i.e., mollusks, barnacles, bryozoans, sponges, tunicates, hydroids, annelids) whether the system is using cooling water on a once-through basis or of the recirculating type. Once-through systems operate by drawing cooling water through the process to be cooled on a one-time basis with a short residence time (usually minutes to hours) and discharging the water directly to a receiving body whereas, recirculation cooling systems require the addition of only a fraction of the system volume as makeup water. Additionally, service water systems such as waste, safety and auxiliary cooling which are often part of these cooling systems are also quite vulnerable to macroinvertebrate fouling, primarily because they do not run continuously, and the conduits are of a small diameter.

The extent and type of macroinvertebrate fouling will depend upon many factors such as the source of the cooling water, the season, the water temperature, the growth rate of the macroinvertebrate, and the linear velocity of the cooling water. Further, because of the large quantities of cooling water used, the locality of the plant will dictate the water's source. A fresh water cooling system will be drawing from a river, a lake, or a well, whereas plants situated along coastal areas will most likely utilize brackish or marine water for their cooling purposes.

Both once-through and recirculating types of cooling water are treated prior to entering the system by screening to remove objects which are large enough that they could damage pumps and heat exchange equipment. This screening does not, however, prevent the passage of early, microscopic life stage or larval stages of the macroinvertebrates, which are the precursors to fouling as growth conditions are usually favorable within these systems. These early life stages of the macroinvertebrates will settle out or attach in low flow areas within the cooling system and grow and accumulate to a fouling size.

For example, mollusks are common macroinvertebrates which can cause fouling problems to marine and fresh water cooling systems. Macrofouling by mollusks, like other groups of fouling mcaroinvertebrates-barnacles, bryozoans, sponges, hydroids, tunicates and annelids-is initiated by the settlement or attachment of larval and/or juvenile stages that are easily entrained into cooling water systems. Fouling caused by the settlement, attachment and/or biogrowth of the macroinvertebrates in the cooling systems and associated service water systems of the industrial plants and utilities which utilize large quantities of water is a major problem causing a variety of deleterious effects to the structure, operation and safety of these systems.

As indicated in the U.S. Nuclear Regulatory Commission 1984 Report entitled "Bivalve Fouling of Nuclear Power Plant Service-Water Systems", the safe operation of a nuclear power plant is a concern because of fouling caused by the Asiatic clam (Corbicula fluminea), the blue mussel (Mytilus edulis) and the American oyster (Crassostrea virginica). This report describes the correlations between the biology of these bivalve mollusks and the design and operation of power plants that allow bivalves to enter and reside within their cooling water systems.

One of the macroinvertebrates controlled by the method of this invention is the mollusk Asiatic clam, Corbicula spp. As indicated in the article entitled "Freshwater Macrofouling and Control with Emphasis on Corbicula" in the December 1983 Proceedings of the Electric Power Research Institute (EPRI), the Asiatic clam has caused significant incidents of macrofouling to fresh water cooling systems of power plants. Another freshwater mollusk, the Zebra mussel (Dreissena polymorph) causes fouling problems to cooling systems in a similar manner as the Asiatic clam. both Dreissena polymorph, causes fouling problems to cooling systems in a similar manner as the Asiatic clam. Both Dreissena and Corbicula have free floating planktonic veliger larvae which allow easy penetration into cooling systems. Similar macrofouling problems plague cooling systems using estuarine, brakish, or marine waters, but with different species of macroinvertebrates.

Fouling control of macroinvertebrates, such as mollusks has been attempted using physical/mechanical and chemical techniques (see, e.g., U.S. Pat. No. 4,328,638), but no truly foolproof combination has been developed.

Chlorine, a commonly used biofouling inhibiting agent, has several limitations with respect to treatment to control macroinvertebrates. Chlorine is very toxic to microorganisms and readily kills them at 1 or 2 mg/liter levels; however, mollusks can survive for a considerable period of time in water containing a much higher level of chlorine because of their anatomic and physiological development relative to microorganisms. Microorganisms must accept the environment they find themselves in and live or die depending upon the nature of the environment. On the other hand, higher animals such as mollusks, and other macroinvertebrates when they find themselves in an environment that is inhospitable, can either more or utilize defense systems to exclude the hostile environment. For example, bivalve mollusks can close their shells to exclude the hostile environment. Bivalve mollusks have very sensitive chemosensors in the mantle lining the edge of their shells and, even when their shells are tightly closed, they can continuously sample the environment to determine when it is safe to open up their shells and start siphoning again. A mollusk immersed in chlorine containing water so that its shell is bleached while will open up after the chlorine level drops and resume its life. As a result, biocides that are sensed by the bivalve mollusk's chemoreceptor organs as life threatening are not effective simply because the mollusk will close its shell until the threat passes. Mollusks can remain closed for days and still live and resume normal activity. For these reasons prolonged exposure to chlorine is required to achieve efficacy. Other limitations of chlorine treatment include the chlorine demand of the cooling water which reduces the potency of chlorine, and the strict environmental regulations being imposed which act to severely limit the discharge of chlorine residues, and in some cases seek to eliminate the use of chlorine entirely.

In addition to chlorine, U.S. Pat. Nos. 4,462,914 and 5,192,451 disclose the use of a high density cationic polymer to control Asiatic clams, Corbicula and Zebra Mussels, respectively. While the polymer appears to be efficacious toward these two mollusks after a six day exposure period, it suffers from some of the same drawbacks as chlorine.

The above-mentioned concerns over the potential environmental impact of biocides is well described by the following excerpt from the December 1983 Proceedings of the Electric Power Research Institute: "Chemical controls have an inherent liability. What can kill inside the power plant may also impact the receiving water body; chemical toxicants are not specific. The perfect chemical would be stable enough to be effective inside the plant, but become non-toxic, via chemical reaction or decay, before or as it entered the receiving water body. So far, no chemical meets these specifications: chlorine and bisulfate/sulfide, which have actually been used in an attempt to control macroinvertebrate fouling, have not been effective alone, or have been successful only under limited conditions. Such a chemical may not exist, but scheduling of application of a chemical at the beginning of scheduled outages may offer a less stringent alternative, because of the possibility of extending holdup times."

U.S. Pat. No. 4,561,983 discloses the use of nitrostyrene compound to control the fouling potential of mollusks. U.S. Pat. No. 4,579,665 discloses the use of a nitrostyrene compound and an alkyl thiocyanate compound to control mollusk fouling potential.

U.S. Pat. No. 4,816,163 discloses a method for controlling the fouling potential of macroinvertebraes, especially mollusks, in an aqueous system which comprises adding to the system an effective controlling amount of a water-soluble alkyl guanidine salt. U.S. Pat. No. 4,857,209 discloses a method for controlling the fouling potential of macroinvertebraes, especially mollusks, in an aqueous system which comprises adding to the system an effective controlling amount of a water-soluble quaternary ammonium salt with detergent properties.

DETAILED DESCRIPTION OF THE INVENTION

The present invention relates to methods for controlling the fouling potential of macroinvertebrates in an aqueous system prone to such fouling comprising adding to the system an effective amount to control fouling of a polymer of a tannin and a cationic monomer.

Tannin, also called tannic acid, occurs in the leaf, branch, bark and fruit of many plants. As disclosed by A. Pizzi in "Condensed Tannin for Adhesives", Ind. Eng. Chem. Prod. Res. Dev. 1982, 21, pages 359–369, the natural tannins can be as "hydrolyzable" tannin and "condensed" tannin. The composition and structure of tannin will vary with the source and the method of extraction, but the empirical structure is given as $C_{76}H_{52}O_{46}$ with many OH groups attached to the aromatic rings. The tannin used in the present invention is a condensed tannin type including but not limited to those derived from Quebracho, Mimosa and Sumac. However, hydrolyzable tannins are also contemplated to be within the scope of this invention.

The present invention relates to methods for controlling the fouling potential of macroinvertebrates in an aqueous system comprising adding to the system a water soluble or dispersible tannin containing polymer composition comprising a copolymer of a tannin and a cationic monomer. In another embodiment of the present invention, the water soluble or dispersible tannin containing polymer composition comprises a polymer of tannin, a cationic monomer and at least one monomer selected from the group consisting of an anionic monomer and a nonionic monomer.

The cationic monomer is selected from a group containing is ethylenically unsaturated quaternary ammonium, phosphonium or sulfonium ions. Typical caflonic monomers are quaternary ammonium salts of dialkylaminoalkyl(meth) acylamides, dialkylaminoalkyl(meth)acrylates and diallyl dialkyl ammonium chloride.

The preferred cationic monomers include but are not limited to methyl chloride quaternary salt of diethylaminoethyl acrylate, dimethyl sulfate salt of diethylaminoethyl acrylate, dimethylaminoethyl acrylate, dimethylaminoethyl methacryl ate, diesthylam inoethyl methacrylate, dimethylaminopropyi methacrylamides, dimethylaminopropyl acryamide, diallyldimethyl ammonium chloride and diallyldiethyl ammonium chloride. The most preferred cationic monomer is methyl chloride quaternary salt of diethylaminoethyl acrylate.

The anionic monomer is selected from the group containing ethylenically unsaturated carboxylic acid or sulfonic acid functional groups. These monomers include but are not limited to acrylic acid, methacrylic acid, vinyl acetic acid, itaconic acid, maleic acid, allylacetic acid, styrene sulfonic acid, 2-acrylamido-2-methyl propane sulfonic acid (AMPS®) and 3-allyloxy-2-hydroxypropane sulfonic acids and salts thereof. The preferred anionic monomer is acrylic acid.

The nonionic monomer is selected from the group of ethylenically unsaturated nonionic monomers which comprise but are not limited to acrylamide, methacrylamide, N-methylolacrylamide, N,N-dimethyl-acrylamide; lower alkyl ($C_1$–$C_6$) esters including vinyl acetate, methyl acrylate, ethyl acrylate, and methyl methacrylate; hydroxylated lower alkyl ($C_1$–$C_6$) esters including hydroxyethyl acrylate, hydroxypropyl acrylate and hydroxyethyl methacrylate; allyl glycidyi ether; and ethoxylated allyl ethers of polyethylene glycol, polypropylene glycol and propoxylated acrylates. The preferred nonionic monomers are allyl glycidyl ether and acrylamide.

The resulting tannin containing polymer contains from D 0 to 80% by weight of tannin, 20 to 90% by weight of cationic monomer, 0 to 30% by weight of nonionic monomer and 0 to 20% by weight of anionic monomer, provided that the resulting tannin containing polymer is still water soluble or dispersible and the total weight % of cationic, nonionic and anionic monomers and tannin adds up to 100%. Preferably, when the cationic monomer and anionic monomer are present together in the tannin containing polymer, the cationic monomer comprises a greater weight percentage than the anionic monomer.

The preferred copolymer of tannin and cationic monomer contains 20 to 80 weight % of tannin. More preferably, the copolymer contains from 30 to 60 weight % of tannin and most preferably, from 30 to 50 weight % of tannin in the copolymer, provided the total weight of tannin and cationic monomer totals 100 weight %. More preferably still, the copolymers have a weight % of 30% tannin and 70% cationic monomer and 50% tannin and 50% cationic monomer. These particular copolymers are most preferred when the tannin is a Mimosa type tannin and the cationic monomer is methyl chloride quaternary salt of dimethylaminoethyl acrylate.

The number average molecular weight of the resulting tannin containing polymer is not critical, as it is still water soluble or dispersible. The tannin containing polymers may be prepared by mixing the desired monomers with tannin and initiating by a free radical initiator via solution, precipitation or emulsion polymerization techniques. Conventional initiators such as azo compounds, persulfates, peroxides and redox couples may be used. The preferred initiators are 2,2'azobis (2-amidinopropane) dihydrochloride, available as V-50 from Wako Chemicals and t-butylhydroperoxide/sodium metabisulfite (t-BHP/NaMBS). These or other initiators may be added at the end of polymerization to further react with any residual monomers.

Chain transfer agents such as alcohol, amine, formic acid or mercapto compounds may be used to regulate the molecular weight of the polymer. The resulting polymer may be isolated by well known techniques including precipitation, etc., or the polymer may simply be used in its aqueous solution.

The reaction temperature is not critical and generally occurs between 20° and 100° C., preferably 40° to 70° C. The pH of the reaction mixture is also not critical and is generally in the range of 2.0 to 8.0. The resulting tannin containing polymers are characterized by C-13 NMR, Brookfield viscosity and percent solids. The procedure for preparing the inventive copolymers may be found in European patent application No. 94304229.1 (publication No. 0630858), the contents of which are wholly incorporated by reference herein.

For purposes of the present invention, the term "macroinvertebrates" is defined to include but is not limited to mollusks such as clams, mussels, oysters, and snails; crustaceans such as barnacles; sponges, hydrozoans; sea anemones; bryozoans; annelids; and tunicates.

The inventive polymers may be added to the desired aqueous system in an amount effective to control macroinvertebrates. For purposes of the present invention, the term "control" is defined to include eradication, inhibiting and/or preventing the growth of macroinvertebrates, and inhibiting and/or preventing the attachment of macroinvertebrates to the surfaces of aqueous systems.

The effective controlling amount of inventive polymer added will of course vary due to factors such as the ambient temperature of the aqueous system, the presence of substances which may in part bind to or inactivate the inventive polymers, as well as, the type and abundance of macroinvertebrates present in the aqueous system being treated. The term "an effective controlling amount" is defined as that amount of inventive polymer which will act to eradicate, inhibit and/or prevent the growth or inhibit and/or prevent the attachment of macroinvertebrates.

Preferably, the inventive polymer may be added to the aqueous system to be treated in an amount ranging from about 1 part to about 100 parts per million parts of water in the aqueous system. More preferably, this range is from about 10 parts to about 20 parts per million parts water.

This invention may be used to control macroinvertebrates in cooling systems for both industrial plants and utilities which are subject to fouling, whether the system is using cooling water on a once-through basis or is of the recirculating type. The present inventors anticipate that the present invention will control macroinvertebrates in ballast water tanks, cooling ponds and basins, intake structure areas such as intake piping conduits of municipal drinking water facilities, and ship reservoirs. The present invention may be used to control all life stages of macroinvertebrates. For example, addition of the inventive polymers to a once-through cooling water system will eradicate larval planktonic forms, small juveniles before they grow to adult size, and adults to control infestation and the consequent build-up on the structural parts of the cooling water system. The destruction of adult macroinvertebrates will also eradicate fouling problems of a more mature nature.

The frequency and the timing of the treatments would be by applying at different treatment intervals ranging from intermittent feedings to applications administered as infrequently as once a year to eradicate the fouling organisms that have colonized or have grown within these systems. Treatment application strategies may include feeding the inventive polymers on a constant basis for a time sufficient to eradicate the fouling organism or treating the aqueous system by dosing the system statically. This would be by stopping the water flow for a time and soaking the water for a time sufficient to control the macroinvertebrates.

Known macroinvertebrate control agents include oxidizing biocides such as chlorine, chlorine dioxide, bromine and ozone which can vary in treatment exposure from short, continuous exposures of one to four weeks to longer exposures lasting several months. However, the use of oxidizing biocides to control macroinvertebrates is significantly being restricted because of stricter environmental regulations. These regulations will severely limit the discharge of chlorine residues, including those forming carcinogen trihalomethane compounds, and in some cases seek to eliminate them entirely.

The inventive polymers of tannin and cationic monomers, as well as those additionally containing nonionic and/or anionic monomers, avoid these difficulties associated with oxidizing biocides. These polymers are relatively inert to aqueous system metallurgy which can range from stainless steel and iron species to copper and its alloys. The polymers are more environmentally acceptable than oxidizing biocides and require significantly shorter exposure periods at surprisingly low concentrations.

The invention will now be further described by the following examples which are included as being illustrative of the invention and should not be construed as limiting the scope thereof.

Experimental

The polymer test solutions were prepared in 3.8-liter glass test chambers containing 3.0 liters of aged dechlorinated tap water. Aliquots of a 5000 mg/L polymer stock solution, which was prepared in deionized water, were added to each test chamber. The test solutions were maintained at 20° C. during the experiment.

Ten individual Zebra Mussels (9–20 mm shell length) were randomly placed into each polymer test solution and in an untreated control. Zebra Mussels used in these experiments were obtained by cutting their byssal threads which anchor them to other mussels and to surfaces of the mussel culturing unit.

The Zebra Mussels were exposed to the polymer solutions for 96 hours followed by 10 days post-exposure to untreated water. The test chambers were covered during the experiment to minimize any possible external disturbances on the Zebra Mussels. The ability of Zebra Mussels to produce byssal threads and reattach to the surface of the test chamber was assessed at the end of the 96-hour polymer exposure and 10-day post exposure. The acute toxicity effects of the various polymer test solution on Zebra Mussels was also assessed during each observation period.

The results of this testing are presented in Tables I, II and III.

TABLE I

Percentage of Zebra Mussels Reattached and
Cumulative Mortality Response
Copolymer of Tannin and AETAC: 42.5%/57.5%

| Concentration (mg/L) | % Reattached After 4 Days | % Reattached After 10 days Post-Exposure | Cumulative % Mortality After 14 Days |
|---|---|---|---|
| 1.0 | 70 | 100 | 0% |
| 2.5 | 100 | 100 | 0% |
| 5.0 | 70 | 100 | 0% |
| 10 | 20 | 70 | 0% |
| 15 | 50 | 100 | 0% |
| 20 | 0 | 70 | 10% |
| Control | 100 | 100 | 0% |

TABLE II

Percentage of Zebra Mussels Reattached and
Cumulative Mortality Response
Copolymer of Tannin and AETAC: 30%/70%

| Concentration (mg/L) | % Reattached After 4 Days | % Reattached After 10 days Post-Exposure | Cumulative % Mortality After 14 Days |
|---|---|---|---|
| 1.0 | 90 | 100 | 0% |
| 2.5 | 90 | 100 | 0% |
| 5.0 | 40 | 100 | 0% |
| 10 | 0 | 100 | 20% |
| 15 | 0 | 100 | 20% |
| 20 | 0 | 100 | 60% |
| Control | 100 | 100 | 0% |

TABLE III

Percentage of Zebra Mussels Reattached and
Cumulative Mortality Response
Copolymer of Tannin and AETAC: 50%/50%

| Concentration (mg/L) | % Reattached After 14 Days | % Reattached After 10 days Post-Exposure | Cumulative % Mortality After 14 Days |
|---|---|---|---|
| 2.5 | 90 | 100 | 0% |
| 5.0 | 60 | 90 | 0% |
| 10 | 90 | 100 | 0% |
| 20 | 20 | 100 | 0% |
| 40 | 10 | 100 | 30% |
| 80 | 0 | 100 | 80% |
| Control | 100 | 100 | 0% |

As demonstrated in Tables I, II, and III, the copolymers of the present invention prevented the Zebra Mussels from reattaching during the 96-hour exposure. However, during the post exposure period, greater than 70% of the surviving mussels reattached.

The copolymers of 42.5:57.5, 30:70, and 50:50 tannin: AETAC inhibited reattachment of greater than 90% of the Zebra Mussels at levels of 20, 10 and 40 mg/L respectively. All of the Zebra Mussels in the control reattached within 96 hours.

The dosage of the copolymers of tannin/cationic monomer required to inhibit reattachment of Zebra Mussels also exhibited low acute toxicity, with less than 30% of the mussels being killed. The results of this testing demonstrate that the copolymers of the present invention will inhibit attachment of Zebra Mussels to surfaces while being non toxic to these organisms.

While this invention has been described with respect to particular embodiments thereof, it is apparent that numerous other forms and modifications of this invention will be obvious to those skilled in the art. The appended claims and this invention generally should be construed to cover all such obvious forms and modifications which are within the true spirit and scope of the present invention.

Having thus described the invention, what we claim is:

1. A method for controlling the fouling potential of macroinvertebrates in an aqueous system selected from the group consisting of once-through or recirculating cooling water systems, ballast water tanks, cooling ponds, intake piping conduits, and ship reservoirs prone to such fouling comprising adding to said system an effective controlling amount of a water soluble or dispersible copolymer comprising a tannin and a cationic monomer wherein said cationic monomer is selected from the group consisting of methyl chloride quaternary salt of diethylaminoethyl acrylate, dimethyl sulfate salt of diethylamntoethyl acrylate, dim ethylaminoethyl acrylate, dimethylaminoethyl methacrylate, diethylaminoethyl methacrylate, dimethylaminopropyl methacrylamide, dimethylaminopropyl acrylamnide, diallyldimethyl arnrnonium chloride, and diallyldiethyl amnmoniumn chloride, and said copolymer comprises from 20 to 80 weight percent tannin and 80 to 20 weight percent cationic monomer based on total weight of said copolymer.

2. The method as claimed in claim 1 wherein said copolymer comprises from 30 to 70 weight percent tannin and 70 to 30 weight percent cationic monomer based on total weight of said copolymer.

3. The method as claimed in claim 1 wherein said tannin is selected from the group consisting of Quebracho, Mimosa, and Sumac.

4. The method as claimed in claim 1 wherein said copolymer further comprises at least one monomer selected from the group consisting of anionic monomers and non-ionic monomers.

5. The method as claimed in claim 4 wherein said anionic monomer is selected from the group consisting of acrylic acid, methacrylic acid, vinyl acetic acid, itaconic acid, malleic acid, allylacetic acid, styrene sulfonic acid, 2-acrylamido-2-methyl propane sulfonic acid and 3-allyloxy-2-hydroxypropane sulfonic acid.

6. The method as claimed in claim 4 wherein said nonionic monomer is selected from the group consisting of acrylamide, methacrylamide, N-methylolacrylamide, N,N-dimethylacrylamide, vinyl acetate, methyl acrylate, ethyl acrylate, methyl methacrylate, hydroxyethyl acrylate, hydroxypropyl acrylate, hydroxyethyl methacrylate, allyl glycidyl ether, and ethoxylated allyl ethers of polyethylene glycol, polypropylene glycol and propoxylated acrylate.

7. The method as claimed in claim 4 wherein said anionic monomer is acrylic acid and said nonionic monomer is selected from the group consisting of allyl glycidyl ether and acrylamide.

8. The method as claimed in claim 1 where said cationic monomer is methyl chloride quaternary salt of diethylaminoethyl acrylate.

9. The method as claim in claim 1 wherein said macroinvertebrate is selected from the group consisting of mollusks, crustaceans, sponges, hydrozoans, sea anemones, bryozoans, annelids, and tunicates.

10. The method as claimed in claim 9 wherein said mollusks are selected from the group consisting of clams, mussels, oysters, and snails.

11. The method as claimed in claim 10 wherein said clams are Asiatic Clams and said mussels are Zebra Mussels.

12. The method as claimed in claim 1 wherein said copolymer is added to said aqueous system in an amount ranging from about 1 parts to about 100 parts per million parts water in said aqueous system.

* * * * *